United States Patent
Hedvati et al.

(10) Patent No.: US 7,528,258 B2
(45) Date of Patent: May 5, 2009

(54) PREPARATION OF OLMESARTAN MEDOXOMIL

(75) Inventors: Lilach Hedvati, Doar Na Hefer (IL); Gideon Pilarsky, Holon (IL)

(73) Assignee: Teva Pharmaceutical Industries Ltd, Petah Tiqva (IL)

( * ) Notice: Subject to any disclaimer, the term of this patent is extended or adjusted under 35 U.S.C. 154(b) by 474 days.

(21) Appl. No.: 11/217,472

(22) Filed: Sep. 2, 2005

(65) Prior Publication Data

US 2006/0069141 A1 Mar. 30, 2006

Related U.S. Application Data

(60) Provisional application No. 60/606,437, filed on Sep. 2, 2004.

(51) Int. Cl.
C07D 257/04 (2006.01)
C07D 405/14 (2006.01)

(52) U.S. Cl. .................................................. 548/253

(58) Field of Classification Search ................ 548/250
See application file for complete search history.

(56) References Cited

U.S. PATENT DOCUMENTS

| | | | |
|---|---|---|---|
| 4,791,210 A | 12/1988 | Bison et al. | |
| 4,870,188 A | 9/1989 | Aldrich et al. | |
| 5,138,069 A | 8/1992 | Carini et al. | |
| 5,236,943 A | 8/1993 | Heitsch et al. | |
| 5,252,753 A | 10/1993 | Russell et al. | |
| 5,264,447 A | 11/1993 | Ohtawa | |
| 5,294,716 A | 3/1994 | Thomas et al. | |
| 5,310,928 A | 5/1994 | Lo et al. | |
| 5,591,762 A | 1/1997 | Hauel et al. | |
| 5,616,599 A | 4/1997 | Yanagisawa | |
| 5,621,134 A | 4/1997 | Katsura | |
| 5,656,650 A | 8/1997 | Weinstock | |
| 5,721,263 A | 2/1998 | Inada et al. | |
| 5,744,612 A | 4/1998 | Koguro et al. | |
| 5,994,348 A | 11/1999 | Ku et al. | |
| 6,040,454 A | 3/2000 | Koguro et al. | |
| 6,111,114 A | 8/2000 | Salibeni | |
| 6,214,999 B1 | 4/2001 | Biard | |
| 6,340,772 B2 | 1/2002 | Toya et al. | |
| 6,861,549 B2 | 3/2005 | Yamada et al. | |
| 6,878,703 B2 | 4/2005 | Sada et al. | |

FOREIGN PATENT DOCUMENTS

| | | |
|---|---|---|
| DE | 197 57 995 A1 | 7/1999 |
| EP | 0 838 458 A1 | 4/1998 |
| EP | 1 555 260 A1 | 7/2005 |
| JP | 6298683 | 10/1994 |
| JP | 753489 | 2/1995 |
| JP | 7053489 | 2/1995 |
| JP | 11292851 | 10/1999 |
| JP | 11302260 | 11/1999 |
| WO | WO 95/32962 | 12/1995 |
| WO | WO 97/49394 | 12/1997 |
| WO | WO 2004/085428 | 10/2004 |

OTHER PUBLICATIONS

Annual Report of Sankyo Research Laboratories 2003, 55.
Larsen et al: "Efficient Synthesis of Losartan, A Nonpeptide Angiotensin II Receptor Antagonist" Journal Of Organic chemistry, vol. 59, No. 21, 1994, 6391-6394.
International Search Report of PCT/US2005/031481, Dec. 29, 2005.
Koike et al. "Olmesartan Medoxomil, A Novel Potent Angiotensin II Blocker", *Annu. Rep. Sankyo Res. Lab*, 55, pp. 1-91, (2003).
Attanasi et al., "Synthesis of Biphenylyltetrazole Derivatives of 1-Aminopyrroles as Angiotensin II Antagonists", *Il Farmaco*, vol. 54, pp. 64-76, (1999).
Physician's Desk Reference 1044-47 (61 ed., 2007). Thomas PDR.
Physician's Desk Reference (2004 ed., 2004) 3000-3001. Thomas PDR.
Carini et al., Nonpeptide angiotensin II receptor antagonists: The discovery of a series of N-(biphenylylmethyl)imidazoles as potent, orally active antihypertensives, J. Med. Chem.. 34, 2525-2547 (1991).
Puchler. et al., "Blood pressure and endocrine effects of single doses of CS-866, a novel angiotensin II antagonist, in salt-restricted hypertensive patients.", J. Hypertens. 1997, 15 (12Pt2), pp. 1809-1812.
Angiotensin II Receptor Antagonists in Perspective, 39-75 (Blackwell Science Inc., Guiseppe Mancia, ed., 2000).
Koike et al, "In vitro and in vivo pharmacology of olmesartan medoxomil, an angiotensin II type AT1 receptor antagonist," J. of Hypertension, 19:S3-S14 (2001).
Jackson, E. K. "Renin and Angiotension", Goodman and Gillman's The Pharmacological Basis of Therapeutics, 809-41 (10th ed. 2001).
"Renin Agniotensin System Antagonists", Drug Facts and Comparison, 514-21 (54th ed. 2000); St. Louis.

*Primary Examiner*—Zinna N Davis
(74) *Attorney, Agent, or Firm*—Kenyon & Kenyon LLP

(57) ABSTRACT

The present invention provides a process for preparing olmesartan medoxomil.

23 Claims, No Drawings

PREPARATION OF OLMESARTAN MEDOXOMIL

This application claims the benefit of U.S. Provisional Patent Application Ser. No. 60/606,437 filed Sep. 2, 2004.

FIELD OF INVENTION

The present invention relates to processes for preparing olmesartan medoxomil.

BACKGROUND OF THE INVENTION

The chemical name for olmesartan medoxomil is 4-(1-hydroxy-1-methylethyl)-2-propyl-1-[[2'-(1H-tetrazol-5-yl)[1,1'-biphenyl]-4-yl]methyl]-1H-imidazole-5-carboxylic acid (5-methyl-2-oxo-1,3-dioxol-4-yl)methyl ester (Merck Index 13th ed.).

The chemical structure of olmesartan medoxomil is:

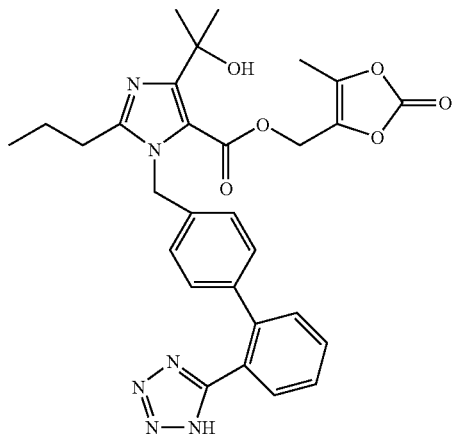

The empirical formula is $C_{29}H_{30}N_6O_6$.

The molecular weight is 558.58.

Olmesartan medoxomil is a prodrug that is hydrolyzed during absorption, and it is a selective $AT_1$ subtype angiotensin II receptor antagonist. Olmesartan medoxomil is disclosed by U.S. Pat. No. 5,616,599 to Yanagisawa et al. It is marketed as BENICAR® in film-coated tablets of 5 mg, 20 mg, and 40 mg for treatment of hypertension in a human.

The synthesis of olmesartan medoxomil (OLM-Mod) per se is illustrated as follows (see also Annu. Rep. Sankyo Res. Lab 2003, 55, 1-91):

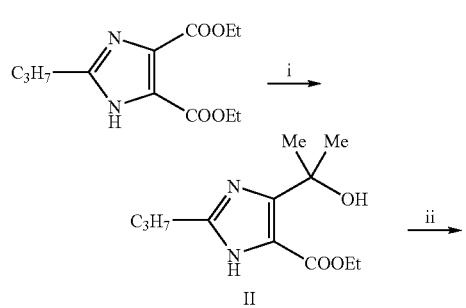

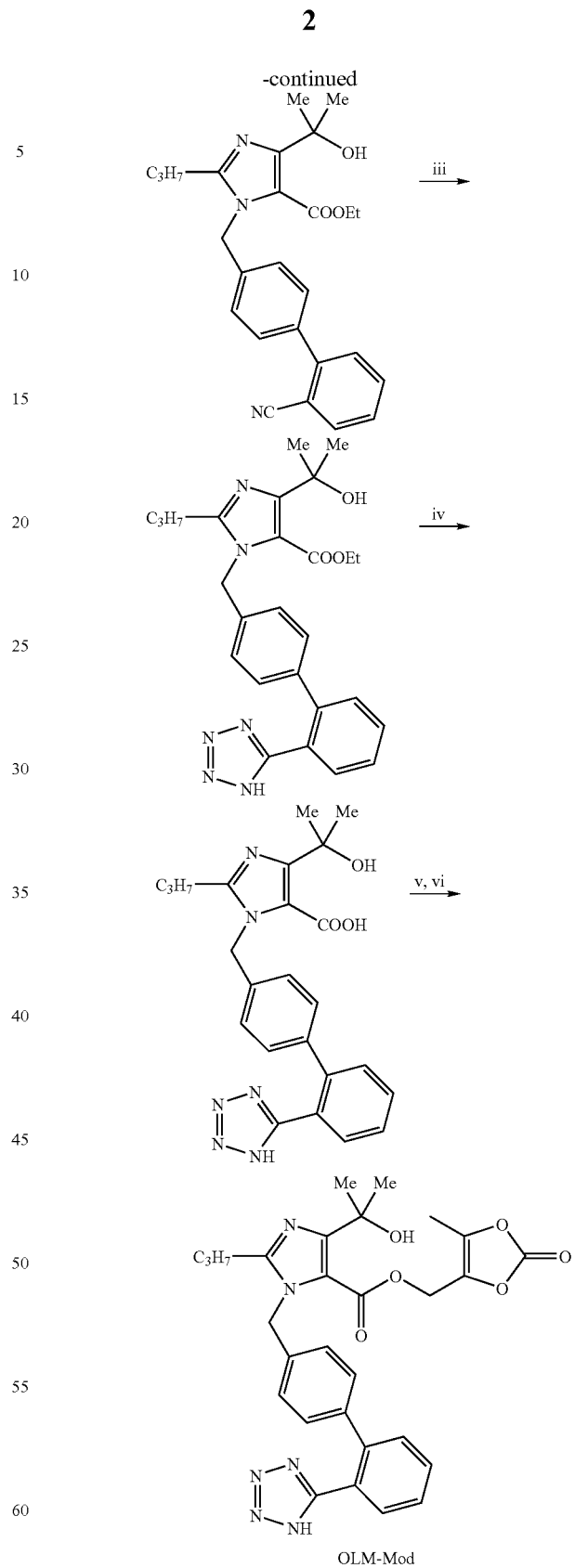

OLM-Mod

Reagents: (i) 4 eq MeMgCl; (ii) 4'-Bromomethylbiphenyl-2-carbonitril, BuOK; (iii) $NaN_3$; (iv) NaOH; (v) $Ph_3CCl/DBU$, then 4-(chloromethyl)-5-methyl-2-oxo-1,3-dioxole; (vi) aq. AcOH The prior art synthetic methods focus on the coupling between the substituted imidazole and the substituted biphenyl methylene bromide. Additional synthetic methods for these olmesartan medoxomil intermediates are described by: JP 11302260, JP 11292851, JP 07053489, JP 06298683, U.S. Pat. No. 5,621,134, EP 838458, DE 19757995, U.S. Pat. No. 6,111,114, and U.S. Pat. No. 6,214,999.

Step (vi) (the deprotection step) of the prior art synthesis is illustrated as follows:

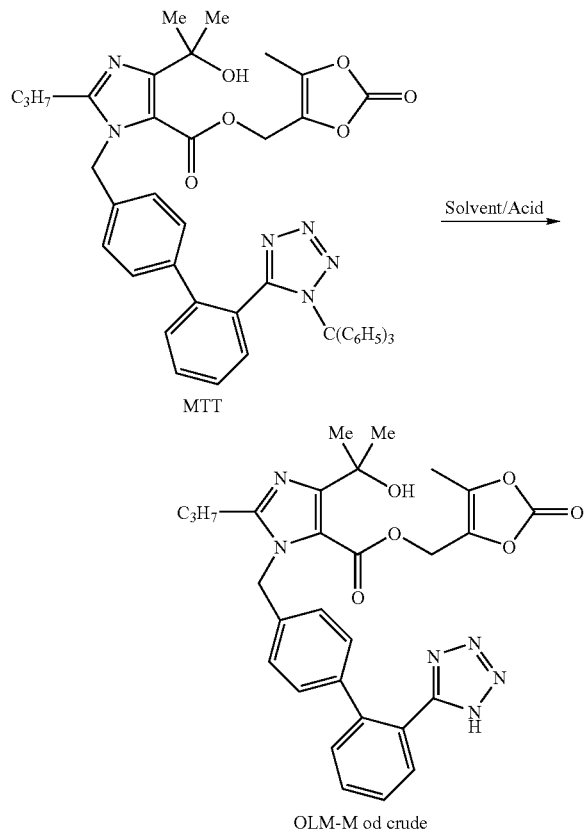

Example 61(b) of the '599 patent discloses a process for preparing crude olmesartan medoxomil from a mixture of trityl olmesartan medoxomil (MTT) and aqueous acetic acid. Col. 176, lines 24-37. Triphenyl carbinol (TPC) is removed, and olmesartan medoxomil is isolated by evaporation.

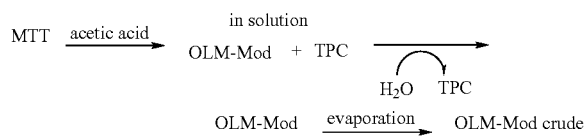

Because of the acidic conditions and the presence of water, the impurity OLM-acid is also formed during the reaction by hydrolysis of the ester bond. The prior art process yields crude olmesartan medoxomil containing 2.2% OLM-acid per area percent HPLC.

There is a need for improved processes for preparing olmesartan medoxomil.

SUMMARY OF THE INVENTION

In one aspect, the present invention provides a process for preparing olmesartan medoxomil including the steps of: contacting trityl olmesartan medoxomil with an acid in a water miscible organic solvent, with or without water, preferably acetone and water, to obtain a solution of olmesartan medoxomil and a precipitate of triphenyl carbinol; separating the precipitate of triphenyl carbinol from the solution of olmesartan medoxomil; and contacting the solution of olmesartan medoxomil with a base to obtain a precipitate of olmesartan medoxomil.

DETAILED DESCRIPTION OF THE INVENTION

The present invention provides a process for preparing olmesartan medoxomil including the steps of: contacting trityl olmesartan medoxomil with an acid in a water miscible organic solvent, with or without water, to obtain a solution of olmesartan medoxomil and a precipitate of triphenyl carbinol; separating the precipitate of triphenyl carbinol from the solution of olmesartan medoxomil; and contacting the solution of olmesartan medoxomil with a base to obtain a precipitate of olmesartan medoxomil.

Preferred water miscible organic solvents include, but are not limited to, acetone, acetonitrile, and t-butanol. Acetone is especially preferred. Preferably, the trityl olmesartan medoxomil is contacted with a mixture of a water miscible organic solvent and water. Most preferably, the trityl olmesartan medoxomil is contacted with a mixture of acetone and water. Preferably, the ratio of water to the water miscible organic solvent, e.g., acetone, is preferably about 1:3 to about 3:1 by volume.

The acid that is contacted with the trityl olmesartan medoxomil removes the triphenyl carbinol to form an acid salt of olmesartan medoxomil. Preferably, the acid is a strong acid having a pH of about 0 to about 4. Suitable acids include, but are not limited to, organic acids such as formic acid, acetic acid, benzoic acid, and oxalic acid; oxoacids such as perchloric acid, chloric acid, chlorous acid, hypochlorous acid, sulfuric acid, sulfurous acid, p-toluene sulfonic acid, nitric acid, nitrous acid, phosphoric acid, and carbonic acid; and binary acids such as hydrofluoric acid, hydrochloric acid, hydrobromic acid, hydrocyanic acid, and hydrosulfuric acid. Hydrochloric acid, p-toluene sulfonic acid, and especially sulfuric acid are preferred. Preferably, the amount of acid is about 2 to about 8 equivalents, more preferably about 3 to about 4 equivalents, and most preferably about 3 equivalents.

When contacting the trityl olmesartan medoxomil with the acid, the temperature is preferably about 10° C. to about 60° C., more preferably about 40° C. In a preferred embodiment, the combination of trityl olmesartan medoxomil, the water miscible organic solvent, and the acid is maintained for about 3 to about 15 hours. Preferably, the combination is maintained for about 4 to about 6 hours, most preferably for about 4 hours.

In a preferred embodiment, prior to separating the triphenyl carbinol, water is added to avoid the formation of undesired by-products. Preferably, the amount of added water is about 2 volumes per gram of trityl olmesartan medoxomil. Precipitation can be perceived visually as a clouding of the solution or formation of distinct particles of the precipitate suspended in the solution or collected at the bottom the vessel containing the solution.

Separating the triphenyl carbinol from the solution can be performed by any means known in the art, such as filtration or centrifugation.

After separating the triphenyl carbinol, the olmesartan medoxomil solution is contacted with a base. Suitable bases include, but are not limited to, alkali and alkaline earth metal hydroxides, carbonates, and hydrogen carbonate salts. Specific exemplary bases include, but are not limited to, sodium hydroxide, potassium hydroxide, calcium hydroxide, magnesium hydroxide, sodium carbonate, potassium carbonate, sodium bicarbonate, potassium bicarbonate, and calcium carbonate. Potassium carbonate and especially sodium bicarbonate are preferred. Preferably, the equivalents of base used is about equal to the equivalents of acid used, that is, the amount of base used is preferably about 0.8 to 1.5 equivalents compared to the amount of acid used. The base preferably increases the pH of the solution, but the solution need not reach a basic pH. After contacting the solution with the base, the solution is preferably maintained at a temperature of about 2° C. to about 25° C., preferably at about room temperature. As used herein, the term "room temperature" refers to a temperature of about 20° C. to 30° C., preferably 20° C. to 25° C. The solution is maintained until olmesartan medoxomil is precipitated.

The precipitate of olmesartan medoxomil can then be recovered by any means known in the art, such as filtration or centrifugation. Olmesartan medoxomil is recovered in its free base form, i.e., the nitrogen on the tetrazole is free.

The reaction progress can be detected by any method known in the art, such as, for example, HPLC, GC, TLC, NMR, and mass spectroscopy.

An exemplary embodiment of the present invention is depicted by the following scheme:

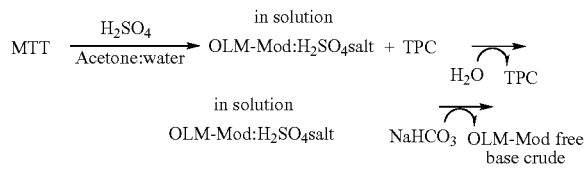

By using the process of the present invention, olmesartan medoxomil can be obtained directly, without the evaporation step required by the prior art process, which is an inconvenient industrial method. See U.S. Pat. No. 5,616,599 Example 61(b). Also, the product of the '599 process is obtained in a gel-like form, which is difficult to handle in an industrial process. In addition to presenting industrial disadvantages, the '599 process achieves a lower yield than that obtained by the present invention. Additionally, the olmesartan medoxomil obtained according to the present invention has a lower amount of the impurity olmesartan acid (OLM-acid). Crude olmesartan medoxomil prepared according to the '599 process contains 2.2% OLM-acid. In contrast, crude olmesartan medoxomil prepared according the present invention contains less than about 1% OLM-acid, e.g., only about 0.89% OLM-acid. All percentages of impurities described herein are provided as area percentage HPLC at 220 nm.

EXAMPLES

Example 1

Preparation of Olmesartan Medoxomil

A 250 round bottom flask was charged with MTT (10 g), acetone/water (2/2 vol.), and 3 eq of $H_2SO_4$. The combination was stirred at room temperature for about 4-6 hrs. Triphenyl carbinol (TPC) was precipitated by adding water and filtered out. $NaHCO_3$ was added to the filtrate, and the mixture was cooled to 5° C. and stirred for 1 hr. Crude olmesartan medoxomil was obtained as white crystals (90% yield).

Example 2

Preparation of Crude Olmesartan Medoxomil

A 1L reactor, equipped with mechanical stirrer and thermometer, was charged with MTT (70 g), acetone (140 ml), water (140 ml), and $H_2SO_4$ (19.47 g). The reactor was heated to 40° C. for 2.5 hrs (at EOR, MTT is LT 1%). Water (140 ml) was added at 40° C., and the reaction was stirred for 1.5 hrs or until MTT is LT 0.1%. After cooling to 15° C. and stirring for 1 hr, the TPC was filtered and washed with water (70 ml).

$NaHCO_3$ was added in portions to the filtrate at room temperature. The reaction mixture was stirred for 1 hr, then filtrated, and the cake was washed with water (140 ml). The solid was dried at 45° C. in a vacuum oven overnight to obtain crude OLM-Mod (98% yield).

Having thus described the invention with reference to particular preferred embodiments and illustrative examples, those in the art can appreciate modifications to the invention as described and illustrated that do not depart from the spirit and scope of the invention as disclosed in the specification. The examples are set forth to aid in understanding the invention but are not intended to, and should not be construed to, limit its scope in any way. The examples do not include detailed descriptions of conventional methods.

What is claimed is:

1. A process for preparing olmesartan medoxomil comprising:
    a) contacting trityl olmesartan medoxomil with an acid in a water miscible organic solvent to obtain a solution of olmesartan medoxomil and a precipitate of triphenyl carbinol;
    b) separating the precipitate of triphenyl carbinol from the solution of olmesartan medoxomil;
    c) contacting the solution of olmesartan medoxomil with a base to obtain a precipitate of olmesartan medoxomil; and
    d) recovering olmesartan medoxomil.

2. The process of claim 1, wherein the trityl olmesartan medoxomil is contacted with the water miscible organic solvent and water.

3. The process of claim 2, wherein the ratio of water to the water miscible organic solvent is about 1:3 to about 3:1 by volume.

4. The process of claim 1, wherein the water miscible organic solvent is selected from the group consisting of acetone, acetonitrile, and t-butanol.

5. The process of claim 4, wherein the water miscible organic solvent is acetone.

6. The process of claim 5, wherein the trityl olmesartan medoxomil is contacted with acetone and water, and the ratio of water to acetone is about 1:3 to about 3:1 by volume.

7. The process of claim 1, wherein the acid has a pH of about 0 to about 4.

8. The process of claim 1, wherein the acid is selected from the group consisting of sulfuric acid, hydrochloric acid, and p-toluene sulfonic acid.

9. The process of claim 8, wherein the acid is sulfuric acid.

10. The process of claim 1, wherein the amount of acid is about 2 to about 8 equivalents.

11. The process of claim 10, wherein the amount of acid is about 3 equivalents.

12. The process of claim 1, wherein step a) is performed at a temperature of about 10° C. to about 60° C.

13. The process of claim 12, wherein step a) is performed at about 40° C.

14. The process of claim 1, wherein prior to step b), the solution of olmesartan medoxomil is maintained for about 3 to about 15 hours.

15. The process of claim 14, the solution of olmesartan medoxomil is maintained for about 4 to about 6 hours.

16. The process of claim 15, wherein the solution of olmesartan medoxomil is maintained for about 4 hours.

17. The process of claim 1, further comprising adding water prior to step b).

18. The process of claim 17, wherein the amount of added water is about 2 volumes per gram of trityl olmesartan medoxomil.

19. The process of claim 1, wherein the base is selected from the group consisting of potassium carbonate and sodium bicarbonate.

20. The process of claim 19, wherein the base is sodium bicarbonate.

21. The process of claim 1, wherein the amount of base used is about 0.8 to 1.5 equivalents compared to the amount of acid used.

22. The process of claim 1, wherein step c) is performed at a temperature of about 2° C. to about 25° C.

23. The process of claim 22, wherein step c) is performed at about room temperature.

* * * * *